United States Patent [19]

McCall

[11] 4,287,338

[45] Sep. 1, 1981

[54] SULFOOXY-PYRIMIDINIUM, -PYRIDINIUM, AND -TRIAZINIUM HYDROXIDE INNER SALTS

[75] Inventor: John M. McCall, Kalamazoo, Mich.

[73] Assignee: The Upjohn Company, Kalamazoo, Mich.

[21] Appl. No.: 128,995

[22] Filed: Mar. 10, 1980

[51] Int. Cl.$^3$ .................. C07D 213/89; C07D 239/48; C07D 251/18; C07D 413/04
[52] U.S. Cl. ................................. 544/123; 544/113; 544/58.6; 544/131; 544/196; 544/197; 544/198; 544/199; 544/205; 544/206; 544/207; 544/295; 544/323; 544/324; 544/327; 544/360; 546/193; 546/257; 546/275; 546/281; 546/307; 260/243.3; 260/244.4; 424/246; 424/248.5; 424/249; 424/250; 424/251; 424/263
[58] Field of Search ............ 544/113, 123, 131, 58.6, 544/323, 324, 327, 295, 360, 196, 197, 198, 199, 205, 206, 207; 546/257, 307, 193, 275, 281; 260/243.3, 244.4

[56] References Cited

U.S. PATENT DOCUMENTS

| | | | |
|---|---|---|---|
| 3,270,014 | 8/1966 | Ursprung et al. | 544/196 |
| 3,382,248 | 5/1968 | Anthony et al. | 544/323 |
| 3,461,461 | 8/1969 | Anthony et al. | 544/323 |
| 3,464,987 | 9/1969 | Ursprung et al. | 544/323 |
| 3,973,016 | 8/1976 | Morrison et al. | 424/246 |
| 4,021,562 | 5/1977 | Lawson et al. | 546/307 |
| 4,080,500 | 3/1978 | Lawson et al. | 544/124 |

Primary Examiner—Henry R. Jiles
Assistant Examiner—R. W. Ramsuer
Attorney, Agent, or Firm—Lawrence T. Welch

[57] ABSTRACT

The present invention provides novel substituted sulfooxy-pyrimidinium, -pyridinium, and -triazinium hydroxide inner salts. These compounds are useful for the treatment of hypertension and peripheral vascular diseases. They are formed by reacting the corresponding aminopyrimidine, aminotriazine, and aminopyridine N-oxides with a latent sulfate source such as pyridinium-sulfur trioxide complex, triethylamine-sulfur trioxide complex, chlorosulfonic acid or chlorosulfuryl chloride.

8 Claims, No Drawings

SULFOOXY-PYRIMIDINIUM, -PYRIDINIUM, AND -TRIAZINIUM HYDROXIDE INNER SALTS

DESCRIPTION

BACKGROUND OF THE INVENTION

This invention relates to novel compositions of matter and methods for preparing them. In particular this invention provides novel sulfooxytriazinium, sulfooxypyrimidinium and sulfooxypyridinium hydroxide inner salts. These compounds are useful in mammals (e.g., humans and domestic animals) for the same pharmacological and therapeutical purposes as the N-oxides from which they are derived, e.g., the treatment of hypertension, congestive heart failure, Raynaud's disease, gangrene, and other peripheral vascular diseases.

The novel compounds of this invention are within a special class of salts known as Inner Salts in which the acidic and basic groups which react to produce the salt linkage are in the same molecule. Such salts may be polar or non-polar.

PRIOR ART

N-oxides corresponding to the novel inner salts are known in the art, and they are useful in the treatment of hypertension. Thus the triazines are disclosed in U.S. Pat. Nos. 3,270,014 and 3,270,015. The pyrimidines are disclosed in U.S. Pat. Nos. 3,461,461, 3,382,248, 3,973,016, 3,464,987, and British Pat. No. 1,486,682. The pyridines are disclosed in U.S. Pat. Nos. 4,021,562, and 4,080,500.

SUMMARY OF THE INVENTION

The present invention particularly provides a compound of the formula II wherein (a) $R_1$ is selected from the group consisting of alkyl of from one to 8 carbon atoms, or $NHR_4$ wherein $R_4$ is hydrogen or alkyl of from one to 4 carbon atoms;

(b) $R_2$ and $R_3$ are the same or different and are hydrogen, alkyl of from one to 8 carbon atoms, with the proviso that if $R_2$ is hydrogen, $R_3$ is not hydrogen or methyl, and vice-versa, alkenyl of from 3-8 carbon atoms (excluding unsaturation at the carbon directly bonded to the nitrogen), phenylalkyl wherein the alkyl portion of the moiety is from one to 3 carbon atoms, cycloalkyl of from 3 to 8 carbon atoms, or $R_2$ and $R_3$ taken together with nitrogen form a heterocyclic moiety selected from the following:

1-aziridinyl, 1-azetidinyl, 1-pyrrolidinyl, 1-piperidinyl, hexahydro-1H-azepin-1-yl, hexahydro-1(2H)-azocinyl, 4-alkylpiperazinyl (wherein the alkyl portion of the moiety is of one to 3 carbon atoms), 4-morpholinyl, 4-thiomorpholinyl, 3,6-dihydro-1(2H)-pyridinyl, 3-pyrrolin-1-yl, 2,3,4,7-tetrahydro-1H-azepine-1-yl, and 3,4,7,8-tetrahydro-1(2H)-azocinyl, said heterocyclic moieties optionally being substituted by one to 3 alkyl groups of from one to 3 carbon atoms, and (c) W and Y are the same or different and are nitrogen or carbon; or the tautomeric or solvated forms thereof.

When W and Y are both carbon, the compounds of the formula II are named as derivatives of pyridine. When W is nitrogen and Y is carbon or vice versa the compounds are named as derivatives of pyrimidine. When both W and Y are nitrogen, the compounds are named as derivatives of 1,3,5-triazine. Thus the compounds of the present invention fall into the classes of the sulfooxytriazinium, sulfooxypyrimidinium, and sulfooxypyridinium hydroxide inner salts. The compounds are named herein basically according to the Chemical Abstracts numbering system. (See Naming and Indexing of Chemical Substances during the Ninth Collective Period (1972–1976), a reprint of Section IV from the Chemical Abstracts Volume 76 Index Guide). Thus if Y and W were carbon, $R_1$ were amino and $R_2$ and $R_3$ were methyl, the compound would be named as the 2,6-diamino-4-(dimethylamino)-1-(sulfooxy)-pyridinium hydroxide inner salt. The numbering starts with the sulfooxy group toward the other ring nitrogen. This system of nomenclature may similarly be used for the triazinium and pyrimidinium derivatives.

Thus, for the triazines, the substituents are numbered starting with the sulfooxy group and following the usual priority system. Thus, if $R_1$ were amino, $R_2$ and $R_3$ were propenyl, and W and Y were nitrogen, the compound would be 2,6-diamino-4-(di-2-propenylamino)-1-(sulfooxy)-1,3,5-triazinium hydroxide, inner salt. If $R_1$ were dimethylamino, and the other substituents were the same, the compound would be named 6-amino-2-(dimethylamino)-4-(di-2-propenylamino)-1-(sulfooxy)-1,3,5-triazinium hydroxide, inner salt.

For the pyrimidines, if Y were carbon, W were nitrogen, $R_1$ were methyl, and $N(R_2)R_3$ formed 1-pyrrolidinyl, the compound would be named 2-amino-6-methyl-4-(1-pyrrolidinyl)-1-(sulfooxy)-pyrimidinium hydroxide, inner salt. Similarly, for the pyridines, where W and Y are carbon, if $R_1$ were methyl, and $N(R_2)R_3$ formed 1-pyrrolidinyl, the compound would be named 2-amino-6-methyl-4-(1-pyrrolidinyl)-1-(sulfooxy)-pyridinium hydroxide, inner salt. If $R_1$ were diethylamino and the other substituents were the same, the compound would be named 6-amino-2-(diethylamino)-4-(1-pyrrolidinyl)-1-(sulfooxy)-pyridinium hydroxide, inner salt. The compounds of this invention may also be represented by the formula IIa. Compounds of the formulas II and IIa are tautomeric with respect to each other.

The tautomeric form of the compounds (formula IIa) are named as the triazines, pyrimidines, and pyridines with a 2-imino substituent, e.g., if $R_1$ were methyl, W was nitrogen, Y was carbon, and $N(R_2)R_3$ formed (4-morpholinyl), the compound of the formula IIa would be named 6-methyl-4-(4-morpholinyl)-1-(sulfooxy)-2(1H)-pyrimidinimine. The compounds will be named and represented herein as inner salts.

The compounds of the present invention may exist as mixtures of the tautomeric forms, the composition of which is dependent on the nature of the substituents and the chemical environment of the compounds. Usually the inner salt form will predominate.

Examples of alkyl are methyl, ethyl, propyl, butyl, pentyl, hexyl, heptyl, octyl, and isomeric forms thereof. Examples of alkenyl are allyl, 1-methylallyl, 2-methylallyl (methallyl), 2-butenyl (crotyl), 3-butenyl, 1,2-dimethylallyl, 1,1-dimethylallyl, 2-ethylallyl, 1-methyl-2-butenyl, 2-methyl-2-butenyl, 3-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-4-hexenyl, and the like. Examples of cycloalkyl are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, and the like. Examples of phenylalkyl are benzyl, phenethyl, 1-phenylethyl, 2-phenylpropyl, and the like.

Examples of heterocyclic moieties within the scope of this invention, in addition to those already mentioned above, are 2-methylaziridinyl, 2-ethylaziridinyl, 2-(n-propyl)aziridinyl, 2,3-dimethylaziridinyl, 2,2-dimethylaziridinyl, 2-methylazetidinyl, 3-methylazetidinyl, 2-isopropylazetidinyl, 2,2-dimethylazetidinyl, 3,3-diethylazetidinyl, 2,4,4-trimethylazetidinyl, 2,3,4-trimethylazetidinyl, 2-methylpyrrolidinyl, 3-ethylpyrrolidinyl, 2-(n-propyl)pyrrolidinyl, 2,3-diethylpyrrolidinyl, 3-isopropylpyrrolidinyl, 2,3,5-trimethylpyrrolidinyl, 3,4-ethylpyrrolidinyl, 2-methylpiperidinyl, 3-methylpiperidinyl, 4-methylpiperidinyl, 3-isopropylpiperidinyl, 4-isopropylpiperidinyl, 2-methyl-5-ethylpiperidinyl, 3,5-dimethylpiperidinyl, 2,4,6-trimethylpiperidinyl, 2,6-dimethyl-4-octylpiperidinyl, 2,3,5-triethylpiperidinyl, 2-ethylhexahydro-1H-azepin-1-yl, 4-isopropylhexahydro-1H-azepin-1-yl, 3-methylhexahydro-1H-azepin-1-yl, 2,4-dimethylhexahydro-1H-azepin-1-yl, 3,3-dimethylhexahydro-1H-azepin-1-yl, 2,4,6-tripropylhexahydro-1H-azepin-1-yl, 2-methylhexahydro-1(2H)-azocinyl, 5-ethylhexahydro-1(2H)-azocinyl, 2,4-diisopropylhexahydro-1(2H)-azocinyl, 3,3-diethylhexahydro-1(2H)-azocinyl, 2,5,8-trimethylhexahydro-1(2H)-azocinyl, 2-ethyl-4-morpholinyl, 2-methyl-5-ethyl-4-morpholinyl, 3,3-dimethyl-4-morpholinyl, 2,6-dimethyl-4-morpholinyl, 4-methyl-1-piperazinyl, 4-isopropyl-1-piperazinyl, 3-ethyl-4-thiomorpholinyl, 2-propyl-3,6-dihydro-1(2H)-pyrindyl and the like. In each of the above examples of heterocyclic moieties, the free valence, and hence the point of attachment to the number 4 carbon atom of the ring, is at the heterocyclic nitrogen atom.

These novel compounds are formed by reacting compounds of the formula I, wherein $R_1$, $R_2$ and $R_3$ are defined as above, in an inert solvent, such as dimethylformamide (DMF) or acetonitrile ($CH_3CN$) with a latent sulfate source such as pyridine-sulfur trioxide complex, triethylamine-sulfur trioxide complex, chlorosulfonic acid, or chlorosulfuryl chloride, as shown by the scheme in Chart A. The term "latent sulfate source", as it is used here, refers to the fact that the reactants such as pyridine-sulfur trioxide complex, triethylamine-sulfur trioxide complex, chlorosulfonic acid or chlorosulfuryl chloride are not sulfate sources of themselves but form a sulfate with the N-1 oxides of the formula I, either directly or in the case of chlorosulfuryl chloride, following workup with an aqueous base such as sodium bicarbonate.

The compounds of this invention optionally are useful in solvated form. The compounds of this invention form complexes with acetonitrile, dimethylformamide, and similar inert solvents. In liquid forms of administration (e.g. intraparenterally) it is optionally preferred to employ the compounds of this invention in solvated form.

The compounds of the formula I are useful for the treatment of hypertension, congestive heart failure, Raynaud's disease, gangrene, and other peripheral vascular diseases. They are administered orally or parenterally (e.g., intravenously, intraperitoneally, or intramuscularly).

Compounds of the formula I are prepared according to the methods described in U.S. Pat. Nos. 3,464,987; 3,382,248; 3,461,461; 3,270,014; 3,910,928; 3,973,016; 4,021,562; and 4,080,500 and British Pat. No. 1,486,682.

The novel compounds of this invention are highly active as antihypertensive agents. Accordingly they are useful for administration to mammals, including humans, whenever it is desirable for medical or veterinary purposes to decrease blood pressure. Humans are the most preferred mammals for administration of these compounds. For oral administration in humans, daily doses of from 0.1 to 100 miligrams per kilogram per day can be employed. An equivalent dosage range for intraperitoneal, intravenous, or intramuscular administration may also be employed. When these novel compounds are administered orally, they are formulated as tablets, capsules, or as liquid preparations, with the usual pharmaceutical carriers, binders, and the like. For intraperitoneal, administration, pharmaceutically acceptable sterile suspensions or solutions are preferred.

The dosage regimen for treating hypertension using the novel compounds of this invention is selected in accordance with a variety of factors, including the type, age, weight, sex, and medical condition of the mammal, the severity of the condition and the particular compound employed. An ordinarily skilled physician or veterinarian will readily determine and prescribe the correct amount of the compound to treat the hypertension. In so proceeding the physician or veterinarian could employ relatively low dosages at first, subsequently increasing the dose until a maximum desired response is obtained.

The novel compounds of the present invention have anti-hypertensive properties surprisingly and unexpectedly more potent than those of the compounds of Formula I. The compounds of Formula I, particularly the pyrimidine derivatives disclosed in U.S. Pat. No. 3,461,461, are also useful for the treatment of congestive heart failure, Raynaud's Disease, gangrene, and other peripheral vascular diseases. The compounds of the present invention, having similar but surprisingly and unexpectedly more potent properties, can also be administered for these purposes, using the dosage regimen described above.

Moreover, because of the more rapid onset of action of the compounds of this invention, they are useful in the treatment of hypertensive crisis. These hypertensive crises occur for example in cases of renal failure (see, e.g., A. J. Elberg, et al., Cardiovascular Medicine, 497–502 (April 1979)). Rapid-acting vasodilating agents are also effective in the treatment of refractory heart failure (see, N. H. Guther, New England Journal of Medicine, Vol. 291, pages 587–592 (1974)). These hypertensive crises have been successfully treated with sodium nitroprusside, a rapid-acting vasodilating agent. (See, G. G. Rowe, et al., American Heart Journal, Vol. 87, pages 83–87, (1974)). The compounds of the present invention can be used to treat hypertensive crises in the same manner. An ordinarily skilled physician or veterinarian will readily determine the proper dosage regimen based on the factors noted above.

The preferred use of the compounds of this invention is as anti-hypertensive agents.

The compounds of this invention may be prepared using the method described above and are used to treat hypertensive crises in the same manner, by intravenous administration. An ordinarily skilled physician or veterinarian will readily determine the proper dosage regimen based on the factors noted above.

DESCRIPTION OF THE PREFERRED EMBODIMENTS

The compounds of this invention may be prepared using the method described above and illustrated in Chart A as shown more particularly in the examples given below.

EXAMPLE 1

2,6-Diamino-4-(1-piperidinyl)-1-(sulfooxy)-pyrimidinium hydroxide, inner salt

Method A

A mixture of 1.00 grams (0.00478 mole) of 2,4-diamino-6-(1-piperidinyl)-pyrimidine-3-oxide, 1.50 grams of pyridine-sulfur trioxide complex in 15 ml of dimethylformamide (DMF) is stirred for 2.5 hrs and then concentrated in vacuo. The residue is warmed on a steam bath and swirled with 60 ml of water for 2 min. The solid product is filtered and washed repeatedly with ether to give, after drying, 0.71 grams of 2,6-diamino-4-(1-piperidinyl)-1-(sulfooxy)-pyrimidinium hydroxide, inner salt. The yield is 51%. The sample is recrystallized from DMF and water, giving a product with a melting point of 188°–189° C.

The C:H:N:S ratio is 37.40:5.19:23.96:11.10.

Method B

A mixture of 1.05 grams of 2,4-diamino-6-(1-piperidinyl)-pyrimidine-3-oxide and 2.78 grams of trimethylamine-sulfur trioxide complex in 50 ml of chloroform and 4 ml of DMF is stirred for 2.5 hrs. The mixture is concentrated, in vacuo. The residue is crystallized from DMF and water to yield 1.20 grams (83%) of the titled product.

Method C

A mixture of 1.00 grams of 2,4-diamino-6-(1-piperidinyl)-pyrimidine-3-oxide, 1.11 grams (0.0096 mole) of chlorosulfonic acid, and 2.47 grams (0.0191 mols) of di-isopropylethylamine in 25 ml of chloroform is stirred overnight. The mixture is concentrated. The residue is stirred with aqueous sodium bicarbonate, filtered, and washed with ether to give 1.2 grams (86%) of white powder which is shown to be pure by TLC. This is recrystallized from DMF and ethyl acetate to yield 0.69 grams of white crystals. A purified sample crystalized from acetonitrile decomposes at 190°–195° C. The structure of the compound formed by this method is shown by x-ray crystallography to be an acetonitrile complex of the titled compound.

EXAMPLE 2

2-amino-6-methyl-4-(1-pyrrolidinyl)-1-(sulfooxy)-pyrimidinium hydroxide, inner salt A mixture of 2.00 grams (0.0103 mole) of 2-amino-4-methyl-6-(1-pyrrolidinyl)pyrimidine-3-oxide and 6.00 grams of trimethylamine-sulfur trioxide complex in 60 ml of chloroform and 6 ml of DMF is refluxed under nitrogen for 2.5 hrs. The mixture is concentrated in vacuo. The residue is triturated with DMF and water to yield 0.73 grams of product (26% yield). This is triturated with acetonitrile to yield 520 mg of 2-amino-6-methyl-4-(1-pyrrolidinyl)-1-(sulfooxy)-pyrimidinium hydroxide, inner salt, which decomposes at 143° C.

The C:H:N ratio is 38.95:5.30:20.79.

EXAMPLE 3

2-amino-6-methyl-4-(4-morpholinyl)-1-(sulfooxy)-pyrimidinium hydroxide, inner salt A mixture of 1.33 grams (0.0063 mole) of 2-amino-4-methyl-6-(4-morpholinyl)pyrimidine-3-oxide and 1.83 gms of pyridine-sulfur trioxide complex in 15 ml of chloroform is stirred at room temperature for 2.5 hr. The mixture is concentrated in vacuo. The residue is triturated with dilute aqueous sodium bicarbonate, water, ether, and finally ethyl acetate. The residue is recrystallized from DMF and water and triturated with dry ethanol. The yield is 0.52 grams (28% yield) of 2-amino-6-methyl-4-(4-morpholinyl)-1-(sulfooxy)-pyrimidinium hydroxide, inner salt, which decomposes at 232°–233° C.

The C:H:N:S ratio is 36.90:5.05:19.57:11.21.

EXAMPLE 4

2,6-diamino-4-(di-2-propenylamino)-1-(sulfooxy)-1,3,5-triazinium hydroxide, inner salt A mixture of 3.00 grams (0.0148 mols) of 2,4-diamino-6-(di-2-propenylamino)-1,3,5-triazine-3-oxide and 4.50 grams of pyridine sulfur trioxide in 3 ml of DMF is stirred for 2 hr. Water (240 ml) is added and the mixture is warmed on a steam bath for 4 min. The white crystals are filtered and dried to yield 3.20 grams of the titled product, a 71% yield. The crystals are homogeneous by TLC. A sample recrystallized from methanol-water decomposes at 258° C.

The C:H:N:S ratio is 35.57:4.72:27.73:10.47.

EXAMPLE 5

2,6-diamino-4-(1-piperidinyl)-1-(sulfooxy)-1,3,5-triazinium hydroxide, inner salt A mixture of 1.00 gram of 2,4-diamino-6-(1-piperidinyl)-1,3,5-triazine-3-oxide, and 1.5 grams of pyridine-sulfur trioxide complex and 15 ml of DMF is stirred for 2.5 hours and then concentrated in vacuo. The residue is warmed on a steam bath and swirled with water for several minutes. The product is filtered and washed repeatedly with ether to give, after drying, 2,6-diamino-4-(1-piperidinyl)-1-(sulfooxy)-1,3,5-triazinium hydroxide, inner salt.

EXAMPLE 6

2,6-diamino-4-(4-thiomorpholinyl)-1-(sulfooxy)-1,3,5-triazinium hydroxide, inner salt A mixture of 1.00 gram of 2,4-diamino-6-(4-thiomorphinyl)-1,3,5-triazine-3-oxide and 3.00 grams of trimethylamine-sulfur trioxide complex in 15 ml of DMF is stirred for 2.5 hours and then concentrated in vacuo. The residue is warmed on a steam bath and swirled with water for several minutes. The product is filtered and washed with ether to give 2,6-diamino-4-(4-thiomorpholinyl)-1-(sulfooxy)-1,3,5-triazinium hydroxide, inner salt.

EXAMPLE 7

2,6-diamino-4-(4-methyl-1-piperazinyl)-1-(sulfooxy)-1,3,5-triazinium hydroxide, inner salt A mixture of 2.00 grams of 2,4-diamino-6-(4-methyl-1-piperazinyl)-1,3,5-triazine-3-oxide and 6.00 grams of trimethylamine-sulfur trioxide complex in 60 ml of chloroform and 6 ml of DMF is refluxed under nitrogen for 2.5 hours. The mixture is then concentrated in vacuo.

The residue is triturated with DMF and water and a second time with acetonitrile to yield the 2,6-diamino-4-(4-methyl-1-piperazinyl)-1-(sulfooxy)-1,3,5-triazinium hydroxide, inner salt.

EXAMPLE 8

2-amino-6-methyl-4-(3,6-dihydro-1-(2H)-pyridinyl)-1-(sulfooxy)-1,3,5-triazinium hydroxide, inner salt A mixture of 1.00 grams of 2-amino-4-methyl-6-(3,6-dihydro-1(2H)-pyridinyl)-triazine-3-oxide, 1.50 grams of chlorosulfonic acid, and 2.5 grams of di-isopropylamine in 25 mls of chloroform is stirred overnight. The mixture is concentrated in vacuo. The residue is stirred with aqueous sodium bicarbonate, filtered and washed with ether to give the crude product. This is recrystallized from DMF and ethyl acetate to yield the purified 2-amino-6-methyl-4-(3,6-dihydro-1-(2H)-pyridinyl)-1-(sulfooxy)-1,3,5-triazinium hydroxide, inner salt.

EXAMPLE 9

2-amino-6-ethyl-4-(diethylamino)-1-(sulfooxy)-1,3,5-triazinium hydroxide, inner salt A mixture of 2.5 grams of 2-amino-4-ethyl-6-(diethylamino)-1,3,5-triazine-3-oxide and 2.0 grams of pyridine-sulfur trioxide complex and 15 mls of DMF is stirred for 2.5 hours and then concentrated in vacuo. The residue is warmed on a steam bath and swirled with water for several minutes. The solid is filtered and washed repeatedly with ether to give, after drying, 2-amino-6-ethyl-4-(diethylamino)-1-(sulfooxy)-1,3,5-triazinium hydroxide, inner salt.

EXAMPLE 10

2-amino-6-(propylamino)-4-(ethylmethylamino)-1-(sulfooxy)-1,3,5-triazinium hydroxide, inner salt A mixture of 1.05 grams of 2-amino-4-(propylamino)-6-(ethylmethylamino)-1,3,5-triazine-3-oxide and 2.75 grams of trimethylaminesulfur trioxide complex in 50 mls of chloroform and 4 mls of DMF is stirred for 2.5 hours. The mixture is concentrated in vacuo. The residue is crystallized from DMF and water to yield 2-amino-6-(propylamino)-4-(ethylmethylamino)-1-(sulfooxy)-1,3,5-triazinium hydroxide, inner salt.

EXAMPLE 11

2,6-diamino-4-(4-thiomorpholinyl)-1-(sulfooxy)-pyrimidinium hydroxide, inner salt A mixture of 1.00 grams of 2,4-diamino-6-(4-thiomorpholinyl)pyrimidine-3-oxide, and 1.50 grams of pyridine-sulfur trioxide complex and 15 mls of DMF is stirred for 2.5 hours and concentrated in vacuo. The residue is warmed on a steam bath and swirled with water for several minutes. The solid product is filtered and washed repeatedly with ether to give, after drying, 2,6-diamino-4-(4-thiomorpholinyl)-1-(sulfooxy)-pyrimidinium hydroxide, inner salt.

EXAMPLE 12

2,6-diamino-4-(benzylmethylamino)-1-(sulfooxy)-pyrimindinium hydroxide inner salt A mixture of 1.00 gm of 2,4-diamino-6-(benzylmethylamino)pyrimidine-3-oxide, 1.15 grams of chlorosulfonic acid and 2.50 grams of di-isopropylethylamine in 25 mls of chloroform is stirred overnight. The mixture is concentrated in vacuo. The residue is stirred with aqueous sodium bicarbonate, filtered, and washed with ether to give 2,6-diamino-4-(benzylmethylamino)-1-(sulfooxy)-pyrimidinium hydroxide, inner salt.

EXAMPLE 13

2,6-diamino-4-(di-2-propenylamino)-1-(sulfooxy)-pyrimidinium hydroxide, inner salt A mixture of 2.00 grams of 2,4-diamino-6-(di-2-propenylamino)pyrimidine-3-oxide and 6.00 grams of trimethylamine-sulfur trioxide complex in 60 mls of chloroform and 6 mls of DMF is refluxed in nitrogen for 2.5 hours. The mixture is then concentrated in vacuo. The residue is triturated with DMF and water and then again with acetonitrile to yield 2,6-diamino-4-(di-2-propenylamino)-1-(sulfooxy)-pyrimidinium hydroxide, inner salt.

EXAMPLE 14

2-amino-6-methyl-4-(3,6-dihydro-1(2H)-pyridinyl)-1-(sulfooxy)-pyrimidinium hydroxide, inner salt A mixture of 1.00 grams of 2-amino-4-methyl-6-(3,6-dihydro-1-(2H)-pyridinyl) pyrimidine-3-oxide, 1.15 grams of chlorosulfonic acid, and 2.50 grams of di-isopropylethylamine in 25 mls of chloroform is stirred overnight. The mixture is concentrated and the residue is stirred with aqueous sodium bicarbonate, filtered, and washed with ether to give 2-amino-6-methyl-4-(3,6-dihydro-1(2H)-pyridinyl)-1-(sulfooxy)-pyrimidinium hydroxide, inner salt.

EXAMPLE 15

2-amino-6-(n-butylamino)-4-(4-morpholinyl)-1-(sulfooxy)pyrimidinium hydroxide, inner salt A mixture of 1.00 grams of 2-amino-4-(n-butylamino-6-(4-morpholino)pyrimidine-3-oxide and 1.50 grams of pyridine-sulfur trioxide complex and 15 mls of DMF is stirred for 2.5 hours and concentrated in vacuo. The residue is warmed on a steam bath and swirled with water for several minutes. The solid product is filtered and washed repeatedly with ether to give, after drying, 2-amino-6-(n-butylamino)-4-(4-morpholino)-1-(sulfooxy)pyrimidinium hydroxide, inner salt.

EXAMPLE 16

2,6-diamino-4-(3-pyrrolin-1-yl)-1-(sulfooxy)-pyrimidinium hydroxide, inner salt.

A mixture of 1.00 grams of 2,4-diamino-6-(3-pyrrolin-1-yl)pyrimidine-3-oxide and 2.75 grams of trimethylamine-sulfur trioxide complex in 50 ml of chloroform and 4 mls of DMF is stirred for 2.5 hours. The mixture is concentrated in vacuo. The residue is crystallized from DMF and water to yield 2,6-diamino-4-(3-pyrrolin-1-yl)-1-sulfooxy-pyrimidinium hydroxide, inner salt.

EXAMPLE 17

2,6-diamino-4-(1-piperidinyl)-1-(sulfooxy)-pyridinium hydroxide, inner salt

A mixture of 1.00 grams of 2,6-diamino-4-(1-piperidinyl)-pyridine-1-oxide and 1.50 grams of pyridine-sulfur trioxide complex in 15 mls of DMF is stirred for 2.5 hours and then concentrated in vacuo. The residue is warmed on a steam bath and swirled with water for several minutes. The solid product is filtered and washed repeatedly with ether to give, after drying, 2,6-diamino-4-(1-piperidinyl)-1-(sulfooxy)-pyridinium hydroxide, inner salt.

EXAMPLE 18

2-amino-6-(methylamino)-4-(4-thiomorpholinyl)-1-(sulfooxy)-pyridinium hydroxide, inner salt A mixture of 1.05 grams of 2-amino-6-(methylamino)-4-(4-thiomorpholinyl)pyridine-1-oxide and 2.75 grams of trimethylamine sulfur trioxide complex in 50 mls of chloroform and 4 mls of DMF is stirred for 2.5 hours. The mixture is concentrated in vacuo. The residue is crystallized from DMF and water to yield 2-amino-6-(methylamino)-4-(4-thiomorpholinyl)-1-(sulfooxy)-pyridinium hydroxide, inner salt.

EXAMPLE 19

2,6-diamino-4-(4-morpholinyl)-1-(sulfooxy)-pyridinium hydroxide, inner salt

A mixture of 2.00 grams of 2,6-diamino-4-(4-morpholinyl)-pyridine-1-oxide and 6.00 grams of trimethylamine-sulfur trioxide complex and 60 mls of chloroform and 6 mls of DMF is refluxed under nitrogen 2.5 hours. The mixture is concentrated in vacuo. The residue is triturated with DMF and water and again with acetonitrile to yield 2,6-diamino-4-(4-morpholinyl)-1-(sulfooxy)-pyridinium hydroxide inner salt.

EXAMPLE 20

2-amino-6-methyl-4-(4-ethyl-1-piperazinyl)-1-(sulfooxy)pyridinium hydroxide, inner salt A mixture of 1.00 grams of 2-amino-6-methyl-4-(4-ethyl-1-piperazinyl)pyridine-1-oxide, 1.15 grams of chlorosulfonic acid, and 2.50 grams of di-isopropylethylamine and 25 mls of chloroform is stirred overnight. The mixture is concentrated in vacuo. The residue is stirred with aqueous sodium bicarbonate, filtered, and washed with ether to give 2-amino-6-methyl-4-(4-ethyl-1-piperazinyl)-1-sulfooxypyridinium hydroxide, inner salt.

EXAMPLE 21

2,6-diamino-4-(2,3,4,7-tetrahydro-1H-azepine-1-yl)-1-(sulfooxy)-1,3,5-triazinium hydroxide, inner salt A mixture of 1.00 grams of 2,4-diamino-6-(2,3,4,7-tetrahydro-1H-azepine-1-yl)-1,3,5-triazine-3-oxide, 1.00 grams of chlorosulfuryl chloride and 2.5 grams of diisopropylethylamine in 25 ml of chloroform is stirred overnight. The mixture is concentrated in vacuo. The residue is stirred with aqueous sodium bicarbonate, filtered and washed with ether to give the crude product. This is recrystallized frin DMF and ethyl acetate to yield the purified 2,6-diamino-4-(2,3,4,7-tetrahydro-1H-azepine-1-yl)-1-(sulfooxy)-1,3,5-triazinium hydroxide, inner salt.

EXAMPLE 22

2-amino-6-methyl-4-(3,4,7,8-tetrahydro-1(2H)-azocinyl)-1-(sulfooxy)-pyridinium hydroxide, inner salt A mixture of 1.00 grams of 2-amino-6-methyl-4-(3,4,7,8-tetrahydro-1-(2H)-azocinyl)-pyridine-1-oxide, 1.00 grams of chlorosulfonic acid, and 2.5 grams of diisopropylamine in 25 ml of chloroform is stirred overnight. The mixture is concentrated in vacuo. The residue is stirred with aqueous sodium bicarbonate, filtered and washed with ether to give the crude product. This is recrystallized from DMF and ethyl acetate to yield the purified 2-amino-6-methyl-4-(3,4,7,8-tetrahydro-1(2H)-azocinyl)-1-(sulfooxy)-pyridinium hydroxide, inner salt.

EXAMPLE 23

6-amino-2-(isopropylamino)-4-(6-methyl-2,3,4,7-tetrahydro-1H-azepine-1-yl)-1-(sulfooxy)-pyridinium hydroxide inner salt.

A mixture of 2.00 grams of 6-amino-2-(isopropylamino)-4-(6-methyl-2,3,4,7-tetrahydro-1H-azepine-1-yl)-pyridine-1-oxide and 6.00 grams of trimethylamine-sulfur trioxide complex in 60 ml of chloroform and 6 ml of DMF is refluxed under nitrogen for 2.5 hrs. The mixture is then concentrated in vacuo. The residue is triturated with DMF and water and a second time with acetonitrile to yield the 6-amino-2-(isopropylamino)-4-(6-methyl-2,3,4,7-tetrahydro-1H-azepine-1-yl)-1-(sulfooxy)pyridinium hydroxide inner salts.

EXAMPLE 24

2,6-diamino-4-(4-methyl-1-piperazinyl)-1-(sulfooxy)-pyrimidinium hydroxide, inner salt A mixture of 1.00 grams of 2,4-diamino-6-(4-methyl-1-piperazinyl)pyrimidine-3-oxide, 1.50 grams of chlorosulfonic acid, and 2.5 grams of di-isopropylethylamine in 25 ml of chloroform is stirred overnight. The mixture is concentrated in vacuo. The residue is stirred with aqueous sodium bicarbonate, filtered and washed with ether to give the crude product. This is recrystallized from DMF and ethyl acetate to yield the purified 2,6-diamino-4-(4-methyl-1-piperazinyl)-1-(sulfooxy)-pyrimidinium hydroxide, inner salt.

EXAMPLE 25

2,6-diamino-4-(dicyclohexylamino)-1-(sulfooxy)-1,3,5-triazinium hydroxide, inner salt A mixture of 2.5 grams of 2,4-diamino-6-(dicyclohexylamino)-1,3,5-triazine-3-oxide and 2.0 grams of pyridine-sulfur trioxide complex in 15 ml of DMF is stirred for 2.5 hr and then concentrated in vacuo. The residue is warmed on a steam bath and swirled with water for several minutes. The solid is filtered and washed repeatedly with ether to give, after drying, 2,6-diamino-4-(dicyclohexylamino)-1-(sulfooxy)-1,3,5-triazinium hydroxide, inner salt.

EXAMPLE 26

2-amino-6-methyl-4-(cyclooctylamino)-1-(sulfooxy)-pyrimidinium hydroxide, inner salt A mixture of 1.00 grams of 2-amino-4-methyl-6-(cyclooctylamino)pyrimidine-3-oxide, 1.00 grams of chlorosulfonic acid, and 2.5 g of di-isopropylethylamine in 25 ml of chloroform is stirred overnight. The mixture is concentrated in vacuo. The residue is stirred with aqueous sodium bicarbonate, filtered and washed with ether to give the crude product. This is recrystallized from DMF and ethyl acetate to yield the purified 2-amino-6-methyl-4-(cyclooctylamino)-1-(sulfooxy)pyrimidinium hydroxide, inner salt.

EXAMPLE 27

2,6-diamino-4-(2-octenylamino)-1-(sulfooxy)-1,3,5-triazinium hydroxide, inner salt A mixture of 2.00 grams of 2,4-diamino-6-(2-octenylamino)-1,3,5-triazine-3-oxide and 6.00 grams of trimethylamine-sulfur trioxide complex in 60 ml of chloroform and 6 ml of DMF is reflexed under nitrogen for 2.5 hr. The mixture is then concentrated in vacuo. The residue is triturated with DMF and water and a second time with acetonitrile to yield the 2,6-diamino-4-(2-octenylamino)-1-(sulfooxy)-1,3,5-triazinium hydroxide, inner salt.

EXAMPLE 28

2,6-diamino-4-((3-phenyl-1-propyl)amino)-1-(sulfooxy)-pyridinium hydroxide, inner salt A mixture of 1.00 grams of 2,6-diamino-4-((3-phenyl-1-propyl)amino)-pyridine-1-oxide, 1.50 grams of chlorosulfonic acid, and 2.5 grams of di-isopropylethylamine in 25 ml of chloroform is stirred overnight. The mixture is concentrated in vacuo. The residue is stirred with aqueous sodium bicarbonate, filtered and washed with ether to give the crude product. This is recrystallized from DMF and ethyl acetate to yield the purified 2,6-diamino-4-((3-phenyl)-1-propyl)amino)-1-(sulfooxy)-pyridinium hydroxide, inner salt.

EXAMPLE 29

2,6-diamino-4-(3-hexenylamino)-1-(sulfooxy)-pyridinium hydroxide, inner salt

A mixture of 2.5 grams of 2,6-diamino-4-(3-hexenylamino)-pyridine-1-oxide and 2.0 grams of pyridine-sulfur trioxide complex and 15 ml of DMF is stirred for 2.5 hr and then concentrated in vacuo. The residue is warmed on a steam bath and swirled with water for several minutes. The solid is filtered and washed repeatedly with ether to give, after drying, 2,6-diamino-4-(3-hexenylamino)-1-(sulfooxy)-pyridinium hydroxide, inner salt.

EXAMPLE 30

Using the methods of the Examples given above, and starting with the appropriate 3-oxide, all of the compounds of this invention are synthesized.

Examples of the triazine derivatives prepared are as follows:

2,6-diamino-4-(hexahydro-1(2H)-azocinyl)-1-sulfooxy-triazinium hydroxide, inner salt;
2-amino-6-methyl-4-(1-piperidinyl)-1-(sulfooxy)-1,3,5-triazinium hydroxide, inner salt;
2,6-diamino-4-(1-azetidinyl)-1-(sulfooxy)-1,3,5-triazinium hydroxide, inner salt;
2,6-diamino-4-(diethylamino)-1-(sulfooxy)-1,3,5-triazinium hydroxide, inner salt;
2,6-diamino-4-(benzylethylamino)-1-(sulfooxy)-1,3,5-triazinium hydroxide, inner salt;
2-amino-6-methyl-4-(di-2-propenylamino)-1-(sulfooxy)-1,3,5-triazinium hydroxide, inner salt;
2,6-diamino-4-(diisopropylamino)-1-(sulfooxy)-1,3,5-triazinium hydroxide, inner salt;
2-amino-6-(n-hexyl)-4-(4-thiomorpholinyl)-1-(sulfooxy)triazinium hydroxide, inner salt;
2,6-diamino-4-(3,6-dihydro-1(2H)-pyridinyl)-1-(sulfooxy)-1,3,5-triazinium hydroxide, inner salt;
2,6-diamino-4-(4-morpholinyl)-1-(sulfooxy)-1,3,5-triazinium hydroxide inner salt.
2-amino-4-(hexahydro-1-(2H)-azocinyl)-6-methyl-1-(sulfooxy)-1,3,5-triazinium hydroxide, inner salt;
2-amino-6-ethyl-4-(1-piperidinyl)-1-(sulfooxy)-1,3,5-triazinium hydroxide, inner salt;
2-amino-6-(n-butyl)-4-(1-azetidinyl)-1-(sulfooxy)-1,3,5-triazinium hydroxide, inner salt;
6-amino-4-(benzylethylamino)-2-(n-pentyl)-1-(sulfooxy)-1,3,5-triazinium hydroxide, inner salt;
6-amino-4-(benzylethylamino)-2-(n-hexyl)-1-(sulfooxy)-1,3,5-triazinium hydroxide, inner salt;
2,6-diamino-4-(ethylamino)-1-(sulfooxy)-1,3,5-triazinium hydroxide, inner salt;
2,6-diamino-4-(n-octylamino)-1-(sulfooxy)-1,3,5-triazinium hydroxide, inner salt;
2,6-diamino-4-(2,3,5-triethylpiperidinyl)-1-(sulfooxy)-1,3,5-triazinium hydroxide, inner salt;
2,6-diamino-4-(4-ethyl-1-piperazinyl)-1-(sulfooxy)-1,3,5-triazinium hydroxide, inner salt;
6-amino-2-ethyl-4-(2-methylhexahydro-1(2H)-azocinyl)-1-(sulfooxy)-1,3,5-triazinium hydroxide, inner salt;
2,6-diamino-4-(3-isopropyl-1-piperdinyl)-1-(sulfooxy)-1,3,5-triazinium hydroxide, inner salt;
6-amino-2-(n-propylamino)-4-(2-ethyl-1-aziridinyl)-1-(sulfooxy)-1,3,5-triazinium hydroxide, inner salt;
2,6-diamino-4-(3-ethyl-4-thiomorpholinyl)-1-(sulfooxy)-1,3,5-triazinium hydroxide, inner salt;
2,6-diamino-4-(cyclopropylamino)-1-(sulfooxy)-1,3,5-triazinium hydroxide inner salt.

Examples of the pyrimidine derivatives prepared are as follows:

2,6-diamino-4-(hexahydro-1(2H)-azocinyl)-1-(sulfooxy))-pyrimidinium hydroxide, inner salt;
2-amino-6-methyl-4-(1-piperidinyl)-1-(sulfooxy)-pyrimidinium hydroxide, inner salt;
2,6-diamino-4-(1-azetidinyl)-1-(sulfooxy)pyrimidinium hydroxide, inner salt;
2,6-diamino-4-(diethylamino)-1-(sulfooxy)pyrimidinium hydroxide, inner salt;
2,6-diamino-4-(benzylethylamino)-1-(sulfooxy)-pyrimidinium hydroxide, inner salt;
2,6-diamino-4-(di-2-butenylamino)-1-sulfooxy)-pyrimidinium hydroxide, inner salt;
2,6-diamino-4-(di-n-propylamino)-1-(sulfooxy)-pyrimidinum hydroxide, inner salt;
2,6-diamino-4-(3-methyl-4-thiomrpholinyl)-1-(sulfooxy)-pyrimidinium hydroxide, inner salt;
2,6-diamino-4-(3,6-dihydro-1(2H)-pyridinyl)-1-(sulfooxy)pyrimidinium hydroxide, inner salt;
2,6-diamino-4-(4-morpholinyl)-1-(sulfooxy)-pyrimidinium hydroxide inner salt.
2-amino-4-(hexahydro-1-(2H)-azocinyl)-6-methyl-1-(sulfooxy)pyrimidinium hydroxide, inner salt;
2-amino-6-ethyl-4-(1-piperidinyl)-1-(sulfooxy)-pyrimidinium hydroxide, inner salt;
6-(n-octyl)-2-amino-4-(1-pyrrolidinyl)-1-(sulfooxy)-pyrimidinium hydroxide, inner salt;
6-amino-4-(4-morpholinyl)-2-(n-pentyl)-1-(sulfooxy)-pyrimidinium hydroxide, inner salt;
6-amino-4-(benzylethylamino)-2-(n-hexyl)-1-(sulfooxy)-pyrimidinium hydroxide, inner salt;
2-amino-4-(di-2-propenylamino)-6-methyl-1-(sulfooxy)-pyrimidinium hydroxide, inner salt;
2,6-diamino-4-(n-octylamino)-1-(sulfooxy)pyrimidinium hydroxide, inner salt;
2,6-diamino-4-(2,3,5-triethylpiperidinyl)-1-(sulfooxy)-pyrimidinium hydroxide, inner salt;
2,6-diamino-4-(dimethylamino)-1-(sulfooxy)-pyrimidinium hydroxide, inner salt;
2,6-diamino-4-(4-ethyl-1-piperazinyl)-1-(sulfooxy)-pyrimidinium hydroxide, inner salt;
6-amino-2-ethyl-4-(2-methylhexahydro-1(2H)-azocinyl)-1-(sulfooxy)pyrimidinium hydroxide, inner salt;
2,6-diamino-4-(3-isopropyl-1-piperidinyl)-1-(sulfooxy)-pyrimidinium hydroxide, inner salt;

6-amino-2-(n-propylamino)-4-(2-ethyl-1-aziridinyl)-1-(sulfooxy)pyrimidinium hydroxide, inner salt;

2,6-diamino-4-(2-ethyl-4-thiomorpholinyl)-1-(sulfooxy)-pyrimidinium hydroxide, inner salt;

6-amino-2-ethyl-4-(3-methylazetidinyl)-1-(sulfooxy)-pyrimidinium hydroxide, inner salt;

6-amino-2-methyl-4-(diethylamino)-1-(sulfooxy)-pyrimidinium hydroxide, inner salt.

2,6-diamino-4-(dicyclohexylamino)-1-(sulfooxy)-pyrimidinium hydroxide, inner salt.

Examples of the pyridinium derivatives prepared are as follows:

2,6-diamino-4-(hexahydro-1(2H)-azocinyl)-1-(sulfooxy)-pyridinium hydroxide, inner salt;

6-amino-2-methyl-4-(1-piperidinyl)-1-(sulfooxy)-pyridinium hydroxide, inner salt;

2,6-diamino-4-(1-azetidinyl)-1-(sulfooxy)-pyridinium hydroxide, inner salt;

2,6-diamino-4-(diethylamino)-1-(sulfooxy)-pyridinium hydroxide, inner salt;

2,6-diamino-4-(1-pyrrolidinyl)-1-(sulfooxy)-pyridinium hydroxide, inner salt;

2,6-diamino-4-(di-n-butylamino)-1-(sulfooxy)-pyridinium hydroxide, inner salt;

2,6-diamino-4-(di-n-propylamino)-1-(sulfooxy)-pyridinium hydroxide, inner salt;

2,6-diamino-4-(4-thiomorpholinyl)-1-(sulfooxy)-pyridinium hydroxide, inner salt;

2,6-diamino-4-(3,6-dihydro-1-(2H)-pyridinyl)-1-(sulfooxy)-pyridinium hydroxide, inner salt;

2,6-diamino-4-(2,3-dimethyl-pyrrolidinyl)-1-(sulfooxy)-pyridinium hydroxide, inner salt;

2-amino-6-methyl-4-(hexahydro-1-(2H)-azocinyl)-1-(sulfooxy)-pyridinium hydroxide, inner salt;

2-amino-6-ethyl-4-(1-piperidinyl)-1-(sulfooxy)-pyridinium hydroxide, inner salt;

2-methyl-6-amino-4-(1-azetidinyl)-1-(sulfooxy)-pyridinium hydroxide, inner salt;

6-amino-2-methyl-4-(diethylamino)-1-(sulfooxy)-pyridinium hydroxide, inner salt;

6-amino-2-isopropyl-4-(4-morpholinyl)-1-(sulfooxy)-pyridinium hydroxide, inner salt;

2,6-diamino-4-(di-n-hexylamino)-1-(sulfooxy)-pyridinium hydroxide, inner salt;

2,6-diamino-4-(dicyclopentylamino)-1-(sulfooxy)-pyridinium hydroxide, inner salt.

Accordingly, each of the various formula II compounds within the scope of this invention is prepared by these means.

FORMULAS

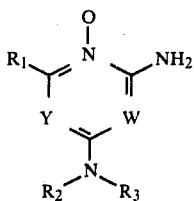

-continued

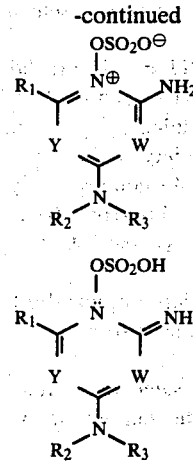

CHART A

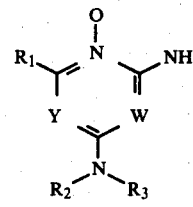

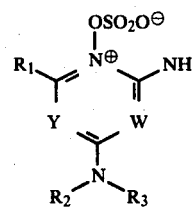

I claim:
1. A compound of the formula II

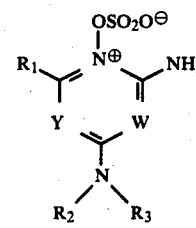

wherein
(a) $R_1$ is selected from the group consisting of alkyl of from one to 8 carbon atoms, or $NHR_4$ wherein $R_4$ is hydrogen or alkyl of from one to 4 carbon atoms;
(b) $R_2$ and $R_3$ are the same or different and are hydrogen, alkyl of from one to 8 carbon atoms, with the proviso that if $R_2$ is hydrogen, $R_3$ is not hydrogen or methyl, and vice-versa, alkenyl of from 3 to 8 carbon atoms (excluding unsaturation at the carbon directly bonded to the nitrogen), phenylalkyl wherein the alkyl portion of the moiety is from one to 3 carbon atoms, cycloalkyl of from 3 to 8 carbon atoms, or $R_2$ and $R_3$ taken together with nitrogen form a heterocyclic moiety selected from the following:

1-aziridinyl, 1-azetidinyl, 1-pyrrolidinyl, 1-piperidinyl, hexahydro-1H-azepin-1-yl, hexahydro-1(2H)-azocinyl, 4-alkylpiperazinyl (wherein the alkyl portion of the moiety is of one to 3 carbon atoms), 4-morpholinyl, 4-thiomorpholinyl, 3,6-dihydro-1(2H)-pyridinyl, 3-pyrrolin-1-yl, 2,3,4,7-tetrahydro-1H-azepine-1-yl, and 3,4,7,8-tetrahydro-1(2H)-azocinyl, said heterocyclic moieties optionally being substituted by one to 3 alkyl groups of from one to 3 carbon atoms, and (c) W and Y are the same or different and are nitrogen or carbon; or the tautomeric or solvated forms thereof.

2. A compound of claim 1 wherein W and Y are carbon.

3. A compound of claim 1 wherein W or Y is nitrogen and the other is carbon.

4. A compound of claim 1 wherein W and Y are both nitrogen.

5. A compound of claim 3 wherein W is nitrogen, Y is carbon, $R_1$ is amino, $R_2$ and $R_3$ with the nitrogen form 1-piperidinyl and the compound is 2,6-diamino-4-(1-piperidinyl)-1-(sulfooxy)pyrimidinium hydroxide, inner salt.

6. A compound of claim 3 wherein W is nitrogen, Y is carbon, $R_1$ is methyl, $R_2$ and $R_3$ with the nitrogen form pyrrolidinyl and the compound is 2-amino-6-methyl-4-(1-pyrrolidinyl)-1-(sulfooxy)-pyrimidinium hydroxide, inner salt.

7. A compound of claim 3 wherein W is nitrogen, Y is carbon, $R_1$ is methyl, $R_2$ and $R_3$ with nitrogen form 4-morpholinyl and the compound is 2-amino-6-methyl-4-(4-morpholinyl)-1(sulfooxyy)-pyrimidinium hydroxide, inner salt.

8. A compound of claim 4 wherein $R_1$ is amino, $R_2$ and $R_3$ are 2-propenyl and the compound is 2,6-diamino-4-(di-2-propenylamino)-1-(sulfooxy)-1,3,5-triazinium hydroxide, inner salt.

* * * * *

UNITED STATES PATENT OFFICE
CERTIFICATE OF CORRECTION

Patent No. 4,287,338            Dated  1 September 1981

Inventor(s)    John M. McCall

It is certified that error appears in the above-identified patent and that said Letters Patent are hereby corrected as shown below:

Column 3, line 35, "-pyridyl and the like" should read -- -pyridinyl and the like --.

Column 16, line 16, "(sulfooxyy)-" should read -- (sulfooxy)- --.

Signed and Sealed this

Fifth Day of July 1983

[SEAL]

Attest:

GERALD J. MOSSINGHOFF

Attesting Officer        Commissioner of Patents and Trademarks